US00PP21233P2

(12) United States Plant Patent
Larsen

(10) Patent No.: US PP21,233 P2
(45) Date of Patent: Aug. 24, 2010

(54) ***OSTEOSPERMUM* PLANT NAMED 'SUNPIX0802'**

(50) Latin Name: *Osteospermum ecklonis*
Varietal Denomination: Sunpix0802

(75) Inventor: Bjarne Nyholm Larsen, Odense (DK)

(73) Assignee: Sunny Gronnegyden APS, Odense (DK)

( * ) Notice: Subject to any disclaimer, the term of this patent is extended or adjusted under 35 U.S.C. 154(b) by 0 days.

(21) Appl. No.: 12/386,338

(22) Filed: Apr. 15, 2009

(51) Int. Cl.
*A01H 5/00* (2006.01)

(52) U.S. Cl. ..... Plt./360

(58) Field of Classification Search ..... Plt./360
See application file for complete search history.

*Primary Examiner*—Annette H Para
(74) *Attorney, Agent, or Firm*—C.A. Whealy

(57) ABSTRACT

A new and distinct cultivar of *Osteospermum* plant named 'Sunpix0802', characterized by its compact and mounded plant habit; freely branching growth habit; daisy-type inflorescences with deep red-colored ray florets; and good garden performance.

2 Drawing Sheets

Botanical designation: *Osteospermum ecklonis.*
Cultivar denomination: 'SUNPIX0802'.

BACKGROUND OF THE INVENTION

The present invention relates to a new and distinct cultivar of *Osteospermum* plant, botanically known as *Osteospermum ecklonis*, and hereinafter referred to by the name 'Sunpix0802'.

The new *Osteospermum* plant is a product of a planned breeding program conducted by the Inventor in Odense, Denmark. The objective of the program is to create and develop new *Osteospermum* cultivars with uniformly mounded plant habit, freely flowering habit and attractive inflorescence coloration.

The new *Osteospermum* plant originated from a cross-pollination by the Inventor in May, 2006 of a proprietary selection of *Osteospermum ecklonis* identified as code number 03.70.003, not patented, as the female, or seed parent with the *Osteospermum ecklonis* 'Shiela', disclosed in U.S. Plant Pat. No. 18,066, as the male, or pollen, parent. The new *Osteospermum* was discovered and selected by the Inventor as a single flowering plant within the progeny of the stated cross-pollination in a controlled greenhouse environment in Odense, Denmark in May, 2007.

Asexual reproduction of the new *Osteospermum* plant by terminal cuttings in a controlled greenhouse environment in Odense, Denmark since November, 2007, has shown that the unique features of this new *Osteospermum* plant are stable and reproduced true to type in successive generations.

SUMMARY OF THE INVENTION

Plants of the new *Osteospermum* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Sunpix0802'. These characteristics in combination distinguish 'Sunpix0802' as a new and distinct cultivar of *Osteospermum:*

1. Compact and mounded plant habit.
2. Freely branching growth habit.

3. Daisy-type inflorescences with deep red-colored ray florets.
4. Good garden performance.

Plants of the new *Osteospermum* differ from plants of the female parent selection in the following characteristics:

1. Plants of the new *Osteospermum* are more compact than and not as vigorous as plants of the female parent selection.
2. Plants of the new *Osteospermum* have smaller leaves than plants of the female parent selection.
3. Plants of the new *Osteospermum* and the female parent selection differ in ray floret color as plants of the female parent selection have pinkish orange-colored ray florets.

Plants of the new *Osteospermum* differ from plants of the male parent, 'Shiela' in the following characteristics:

1. Plants of the new *Osteospermum* are more compact than and not as vigorous as plants of 'Shiela'.
2. Plants of the new *Osteospermum* have smaller inflorescences than plants of 'Shiela'.
3. Plants of the new *Osteospermum* and 'Shiela' differ in ray floret color as plants of 'Shiela' have orange red-colored ray florets.

Plants of the new *Osteospermum* can be compared to plants of *Osteospermum ecklonis* 'Sunny Mary', disclosed in U.S. Plant Pat. No. 16,389. In side-by-side comparisons conducted in Odense, Denmark, plants of the new *Osteospermum* differed from plants of 'Sunny Mary' in the following characteristics:

1. Plants of the new *Osteospermum* were more compact and less vigorous than plants of 'Sunny Mary'.
2. Plants of the new *Osteospermum* and 'Sunny Mary' differed in ray floret color as plants of 'Sunny Mary' had red purple-colored ray florets.

BRIEF DESCRIPTION OF THE PHOTOGRAPHS

The accompanying photographs illustrate the overall appearance of the new *Osteospermum.* These photographs shows the colors as true as it is reasonably possible to obtain in colored reproductions of this type. Colors in the photographs may differ slightly from the color values cited in the detailed botanical description which accurately describe the colors of the new *Osteospermum.*

The photograph on the first sheet comprises a side perspective view of a typical flowering plant of 'Sunpix0802'.

The photograph on the second sheet is a close-up view of a typical inflorescence of 'Sunpix0802'.

DETAILED BOTANICAL DESCRIPTION

The aforementioned photographs, following observations and measurements describe plants grown in Bonsall, Calif. during the spring in a polyethylene-covered greenhouse and under conditions and practices which approximate those generally used in commercial *Osteospermum* production. During the production of the plants, day temperatures averaged 24° C. and night temperatures averaged 14° C. Plants were pinched one time. Plants were 16 weeks old when the photographs and description were taken. In the following description, color references are made to The Royal Horticultural Society Colour Chart, 2001 Edition, except where general terms of ordinary dictionary significance are used.

Botanical classification: *Osteospermum ecklonis* 'Sunpix0802'.

Parentage:

*Female, or seed, parent.*—Proprietary selection of *Osteospermum ecklonis* identified as code number 03.70.003, not patented.

*Male, or pollen, parent.*—*Osteospermum ecklonis* 'Shiela', disclosed in U.S. Plant Pat. No. 18,066.

Propagation:

*Type.*—Terminal vegetative cuttings.

*Time to initiate roots, summer.*—About ten days at 18° C.

*Time to initiate roots, winter.*—About twelve days at 18° C. to 20° C.

*Time to produce a rooted cutting, summer.*—About three weeks at 18° C. to 20° C.

*Time to produce a rooted cutting, winter.*—About four weeks at 18° C.

*Root description.*—Medium in thickness, fibrous; light tan in color.

*Rooting habit.*—Freely branching; moderately dense.

Plant description:

*Plant form/growth habit.*—Compact, upright and mounded plant habit.

*Plant height.*—About 27 cm.

*Plant diameter.*—About 42 cm.

*Lateral branches.*—Quantity per plant: Freely branching habit, about 30 lateral branches develop per plant; pinching enhances branching. Length: About 13.5 cm.

*Foliage description.*—Arrangement/quantity: Alternate, simple; leaves sessile; about 16 leaves per lateral branch. Length: About 5.9 cm. Width: About 2.6 cm. Shape: Oblanceolate. Apex: Obtuse. Base: Narrowly cuneate. Margin: Entire with infrequent deep indentations. Texture, upper and lower surface: Slightly pubescent. Color: Developing leaves, upper surface: Close to 137B. Developing leaves, lower surface: Close to 137D. Fully expanded leaves, upper surface: Close to 137A; venation, close to 144A. Fully expanded leaves, lower surface: Close to 137C; venation, close to 143B.

Inflorescence description:

*Appearance.*—Daisy-type inflorescences; inflorescences positioned above and beyond the foliage; inflorescences terminal and axillary. Disc and ray florets developing acropetally on a capitulum. Moderately freely flowering habit; about five inflorescences developing per lateral branch.

*Fragrance.*—Moderately fragrant.

*Flowering response.*—Plants of the new *Osteospermum* flower continuously from February to September; inflorescences last about two to three weeks on the plant; inflorescences persistent.

*Inflorescence bud.*—Height: About 1 cm. Diameter: About 8 mm. Shape: Spherical. Color: Close to 144B.

*Inflorescence size.*—Diameter: About 6 cm. Depth (height): About 2 cm. Disc diameter: About 2.1 cm. Receptacle diameter: About 7 mm. Receptacle height: About 4 mm.

*Ray florets.*—Length: About 2.7 cm. Width: About 5 mm. Shape: Narrowly oblanceolate. Apex: Obtuse. Margin: Entire. Texture, upper and lower surfaces: Smooth, glabrous. Number of ray florets per inflorescence: About 32 in one to two whorls. Color: When opening, upper surface: Close to 60B; towards the apex, streaked with close to 38C. When opening, lower surface: Close to 77B; faint streaks, close to 23D. Fully opened, upper surface: Close to 60B; with development, color becoming closer to 59A. Fully opened, lower surface: Close to 185A.

*Disc florets.*—Shape: Tubular; apex, five-pointed. Length: About 7 mm. Diameter: About 1 mm. Number of disc florets per inflorescence: About 200. Color: Immature: Apex, close to N186C; mid-section and base, close to 62D. Mature: Apex, close to N186D; mid-section and base, close to 62D. With development, apex, close to 187A; mid-section and base, close to 181D.

*Phyllaries.*—Quantity per inflorescence: About 28. Length: About 8 mm. Width: About 1 mm. Shape: Lanceolate. Apex: Acute. Margin: Entire. Texture: Slightly pubescent. Color, upper and lower surfaces: Close to 144B.

*Peduncles.*—Length, terminal peduncle: About 4.7 cm. Length, axillary peduncle: About 3.3 cm. Diameter: About 2 mm. Strength: Moderate. Aspect, terminal peduncle: Erect. Aspect, axillary peduncle: About 10° from vertical. Texture: Pubescent. Color: Close to 144B.

*Reproductive organs.*—Androecium: Present on disc florets only. Anther shape: Lanceolate. Anther length: About 2 mm. Anther color: Close to 187A. Pollen amount: Moderate. Pollen color: Close to 24B. Gynoecium: Present on both ray and disc florets. Pistil length: About 3 mm. Stigma shape: Two-branched. Stigma length: About 2 mm. Stigma color: Close to N77A. Style length: About 2 mm. Style color: Close to 70C.

*Seeds/fruits.*—Seed and fruit development have not been observed on plants of the new *Osteospermum*.

Disease/pest resistance: Plants of the new *Osteospermum* have not been shown to be resistant to pathogens and pests common to *Osteospermums*.

Garden performance: Plants of the new *Osteospermum* have been observed to have good garden performance and to tolerate rain, wind and temperatures ranging from about −4° C. to about 30° C.

It is claimed:

1. A new and distinct *Osteospermum* plant named 'Sunpix0802' as illustrated and described.

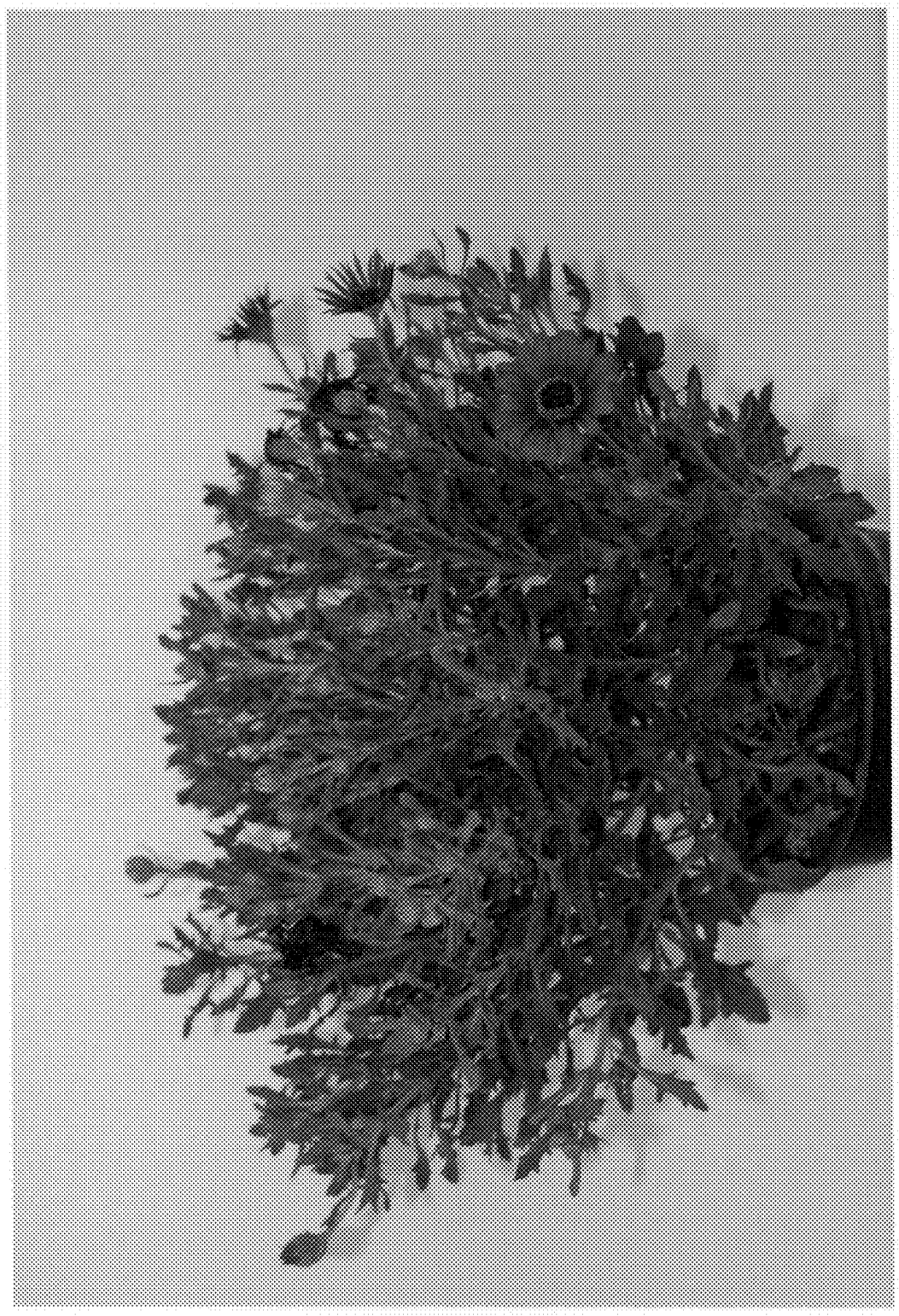

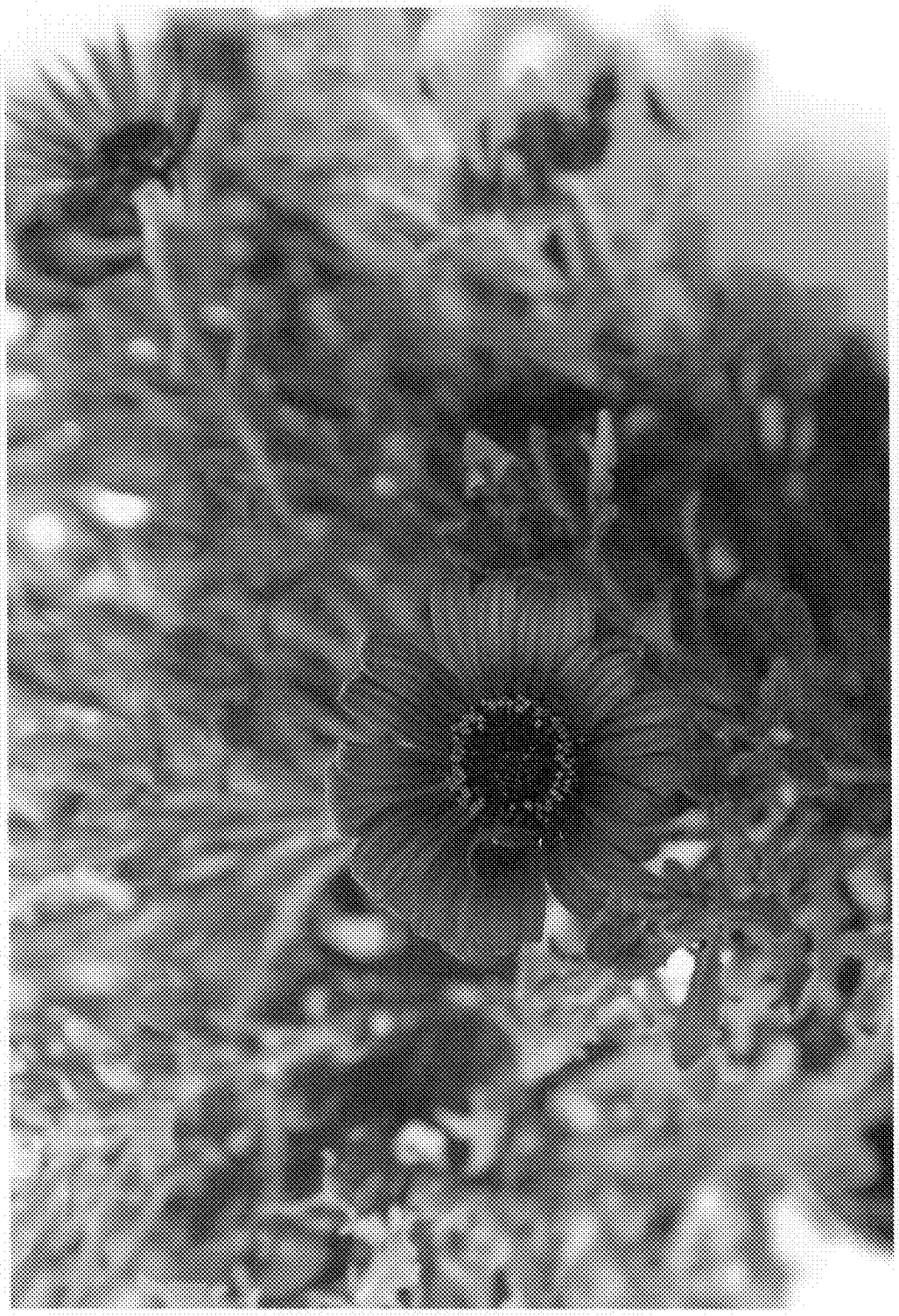

* * * * *